(12) United States Patent
Van den Akker et al.

(10) Patent No.: US 7,210,479 B2
(45) Date of Patent: May 1, 2007

(54) HYPEROXIC BREATHING SYSTEM

(76) Inventors: Erik Van den Akker, 47380 Via Koron, La Quinta, CA (US) 92253; Greg Martin, 595 Talus Wav, Reno, NV (US) 89503; John R. Howitt, 35 N. Edison, Suite 37, Reno, NV (US) 89502

( * ) Notice: Subject to any disclaimer, the term of this patent is extended or adjusted under 35 U.S.C. 154(b) by 40 days.

(21) Appl. No.: 10/984,015

(22) Filed: Nov. 8, 2004

(65) Prior Publication Data

US 2005/0115566 A1 Jun. 2, 2005

Related U.S. Application Data

(60) Provisional application No. 60/518,569, filed on Nov. 7, 2003, provisional application No. 60/531,088, filed on Dec. 19, 2003, provisional application No. 60/532,311, filed on Dec. 22, 2003.

(51) Int. Cl.
*A61M 16/00* (2006.01)
*A61M 16/20* (2006.01)

(52) U.S. Cl. .............................. 128/204.26; 128/204.24

(58) Field of Classification Search ........... 128/205.24, 128/200.25, 201.23, 201.28, 204.18, 204.25, 128/204.26, 204.28, 204.29, 205.13, 205.14; 137/115.11

See application file for complete search history.

(56) References Cited

U.S. PATENT DOCUMENTS 4,141,356 A * 2/1979 Smargiassi ............. 128/204.23

* cited by examiner

*Primary Examiner*—Justine R. Yu
*Assistant Examiner*—Shumaya Ali
(74) *Attorney, Agent, or Firm*—Ian F. Burns & Associates; Ian F. Burns (57) ABSTRACT

A controlled enhanced-oxygen (hyperoxic) breathing system involving an oxygen source, a control valve system and a breathing interface, is disclosed. The control valve system may include a demand flow valve and a venturi valve arranged to introduce ambient air into an oxygen stream to provide a desired level of oxygen in the resultant hyperoxic air stream. Alternatively, the control valve system may include a nitrogen-removal unit, such as nitrogen scrubber, to increase the oxygen content above that of ambient air. The control valve system may further include a one-way flow valve and may further be joined to a plenum for storing hyperoxic air. The hyperoxic breathing system is typically connected to a breathing mask for use by an individual undergoing exercise or physical training activities.

8 Claims, 5 Drawing Sheets

HYPEROXIC BREATHING SYSTEM

CROSS-REFERENCE TO RELATED APPLICATIONS

This application claims priority to U.S. provisional patent application Nos. 60/518,569 filed on Nov. 7, 2003; 60/531,088 filed on Dec. 19, 2003; and 60/532,311 filed on Dec. 22, 2003. The aforementioned are hereby expressly incorporated by reference in their entirety.

BACKGROUND OF THE INVENTION

Endurance exercise performance has been shown to be limited by oxygen availability to the working muscles. Work rates of individuals partaking in endurance exercise can be increased when oxygen delivery to the working muscle is increased (hyperoxia). Furthermore, cyclists who trained under hyperoxia improved their ability to perform high intensity exercise significantly more than did cyclists who trained under similar conditions but with normal oxygen availability (normoxia).

Regular vigorous exercise has been recognized as a useful therapy for treating patients who suffer from maladies such as cardio- and peripheral vascular diseases. Unfortunately, the effects of many of these diseases prevent prolonged vigorous exercise by restricting the blood flow and thus the rate of oxygen delivery to the working muscle. By increasing the concentration of oxygen in the inspired air, oxygen delivery to the working muscle can be increased, thereby increasing the exercising capacity of these patients and improving the therapeutic use of exercise.

In addition, increasing exercising work rates via hyperoxia increases the rate of caloric (energy) expenditure by the exercising individual. Increasing oxygen availability during exercise has also been shown to increase the body's reliance on stored body fat as an energy source. The rate of obesity among Americans is estimated at 25% and many others are overweight to the point that their health may be impaired. Obesity and high body fat to lean body mass ratios have been associated with increased risk of cardiovascular disease, stroke, hypertension, adult onset diabetes, arthritis and degenerative joint disease. Maintaining healthy weight and body composition is a function of maintaining caloric balance (a balance between caloric consumption and caloric expenditure). Losing weight requires an individual to maintain a negative caloric balance (consume fewer calories than they expend). Traditional methods of attaining negative caloric balance include calorie restrictive diets, increased caloric expenditure through exercise, and a combination of these strategies.

Total caloric expenditure from exercise is determined primarily by the total work performed. The amount of work performed during exercise can be manipulated by either increasing the duration of the exercise period or by increasing the rate at which work is performed. However, work rate is limited by the metabolic capacity of an individual. A primary limiting factor in the metabolic capacity of an individual is the ability to deliver adequate amounts of oxygen to their working muscle. Oxygen is a key ingredient in the process of transforming energy from food and bodily energy stores, for example, fat and carbohydrates, into energy that can be used to fuel muscular contractions. This process of combining oxygen with food to liberate energy is known as aerobic metabolism. When working muscles are supplied with adequate amounts of oxygen, their energy requirements can be met and exercise can be maintained for extended periods of time. Increasing the supply of oxygen to the working muscle increases the rate of aerobic metabolism and the rate of work that can be maintained by the individual. However, when exercising work rates create energy demands that exceed a person's ability to supply energy through aerobic metabolism, the person will fatigue quickly and must either stop exercising or reduce their work rate. Thus, the rates of work and caloric expenditure during exercise can be affected by the availability of oxygen to the working muscle of the individual.

Another benefit of increasing oxygen availability to the exercising individual centers on the use of stored body fat as a source of energy. The two primary sources of energy used by the human body to fuel muscular contractions are carbohydrates and fats. Liberating stored energy from fats requires more oxygen than liberating an equal amount of energy from carbohydrates. Typically, the more oxygen that is available to the working muscle, the more the muscle will rely on fat to meet its energy needs. Thus, in addition to increasing work rate and caloric expenditure, increasing oxygen availability during exercise will increase the body's reliance on fat as an energy source.

The significant aspects of greater fat usage during exercise are twofold: firstly, the catabolism of stored body fat during exercise reduces body fat mass and lowers the ratio of body fat mass to lean body mass. Secondly, greater use of stored body fat reduces the reliance on bodily stores of carbohydrate to fuel muscular contractions. Maintaining adequate stores of carbohydrate is an important aspect of appetite control. The body relies on its stores of carbohydrates for a variety of tasks including the maintenance of blood sugar levels. As bodily stores of carbohydrate drop, so do the levels of sugar in the blood. Low blood sugar has been identified as a major contributor to the stimulation of appetite. Thus, a greater reliance on fat during exercise allows the body to preserve carbohydrate stores, maintain blood sugar levels and suppress appetite following exercise.

Delivery of oxygen to the working muscle has been shown to be affected by the exercising environment. The earth's atmosphere contains 21% oxygen, an oxygen level that is referred to as "normoxic" or "normoxia". Hyperoxia refers to a condition in which the oxygen levels are higher than 21 percent. Hyperoxic conditions that feature oxygen concentrations that are substantially higher than 21% result in greater oxygen delivery to and higher oxygen consumption by working muscle. The proposed breathing system of the present invention is considered to provide a method to combat obesity and maintain healthy weights and body compositions in individuals.

Devices designed to provide mixtures of gases with variable concentrations of oxygen are known. U.S. Pat. No. 5,915,834 discloses a system using a controller to dial in desired amounts of oxygen and air from gas supply sources through an inlet into a mixing plenum to provide an oxygen mixture. U.S. Pat. No. 5,372,129 discloses an oxygen dilution device for use by patients with respiratory problems, where the device includes a hollow diluter body having a dilution chamber and a vent chamber. U.S. Pat. No. 3,830,257 discloses a device for providing a mixture of air and oxygen to a respiratory mask, where the device includes multiple chambers in communication with the mask and responsive to each other to provide a constant ratio of air to oxygen to the mask. U.S. Pat. No. 3,875,957 discloses an oxygen-air diluter device for breathing apparatus used in high altitude and space flights, where the device includes a casing having oxygen and ambient air inlets and a differential pressure diaphragm, and is designed to control air flow to provide normal air dilution, 100 percent oxygen and pressure breathing. None of the aforementioned devices discloses or suggests use of the control valve system of the proposed breathing system of the present invention as a way to conveniently provide hyperoxic air mixtures for breathing.

Devices designed to provide hyperoxic gas to individuals are widely used in hospital, clinical and home settings. However, most devices do not provide breathing gases at rates that are required during exercise. Other devices designed for exercising individuals have a number of deficiencies that are overcome by the breathing system of the present invention. These deficiencies are as follows:

First, using gas mixtures with oxygen concentrations greater than atmospheric air but less than pure oxygen requires the purchase of cylinders containing premixed gases. While this is possible, it is far more expensive than the cost of equal amounts of pure oxygen and air. Secondly, gases from commercial cylinders are void of moisture and breathing a dry gas mixture during vigorous exercise results in the drying of the upper respiratory tract and the production of mucous causing discomfort and coughing. Thirdly, maintaining the proper rate of gas flow from the oxygen cylinder requires frequent adjustments to the pressure regulator. In current model regulators, the design is such that it is very difficult for the user of the device to adjust the flow of gas from the oxygen cylinder while exercising. Thus, a second individual is needed to monitor and adjust the flow rate from the oxygen cylinder. Finally, in current devices, air flow to the subject is dependent on flow rates from the compressed gas cylinder. In the event that the gas cylinder should empty, air flow to the user stops abruptly. While removing the subject from the device can quickly restore air flow, the brief period in which air flow to the user is stopped is unsettling and does not promote optimal use of hyperoxic training.

The proposed breathing system of the present invention overcomes the aforementioned deficiencies by use of a control valve system to provide an air mixture containing 25–90 volume percent oxygen to the user and at rates that are similar to the ventilation rate of the user. Use of the control valve system of the breathing system of the present invention eliminates the need to purchase pre-mixed breathing gases and the need for manual flow adjustments from compressed oxygen gas cylinders. In addition, lack of moisture in the commercially available gas mixture is overcome by the use of atmospheric air in the breathing system of the present invention.

SUMMARY OF THE INVENTION

The present invention provides a controlled enhanced-oxygen (hyperoxic) breathing system comprising a control valve system coupled to an oxygen source (for example, compressed oxygen gas cylinder) and a breathing interface coupled to the control valve system, where the control valve system may further include a demand flow valve and a venturi valve configured to introduce ambient air into an oxygen stream provided by the oxygen source.

A breathing mask is typically attached to the breathing interface for use by a breathing subject, such as someone exercising or performing physical training activities. Typically, the demand flow and venturi valves are connected in series and the control valve system may further include a one-way flow valve located between the venturi valve and the breathing interface.

In one embodiment, the present invention includes a plenum or enclosed space configured to contain the hyperoxic air mixture, where the plenum may be coupled to the control valve system via the one-way flow valve and a gas transport line between the demand flow valve and the plenum; typically, the plenum comprises a diaphragm and the gas transport line provides communication between the diaphragm of the plenum and the demand flow valve. The plenum may further include an exhaust valve for relieving pressure within the plenum, for example, when a breathing subject exhales during exercise using the hyperoxic breathing system of the present invention. The plenum may further include an emergency valve to provide access to ambient air, for example, when the oxygen supply is depleted and the flow of air may be insufficient for breathing comfortably.

In another embodiment, the present invention includes a pressure regulator coupled to the oxygen source and located between the oxygen source and the control valve system. The pressure regulator is typically used to provide step down pressures from the high pressure available with most compressed oxygen gas cylinders. In another embodiment, the present invention includes a control linkage associated with the pressure regulator and configured to control oxygen flow from the oxygen source. For example, in the case where the control linkage comprises a cable, an exercising subject would be able to open and close the pressure regulator from a distance, such as from a bicycle or other type of exercising device.

In a further embodiment of the present invention, a second plenum may be located between the first plenum and the breathing interface where a second gas transport connection having a second one-way flow valve may be used to connect the two plenums. In this case, the second plenum typically includes the exhaust or emergency valves rather than these features being included with the first plenum.

In another embodiment, the hyperoxic breathing system of the present invention comprises an air source, a control valve system and a breathing interface coupled to the control valve system, where the control valve system includes a demand flow valve and a nitrogen-removal unit. In this case, the nitrogen-removal unit replaces the venturi valve component discussed in the aforementioned embodiments. Whereas the venturi valve provided mixing of ambient air with a pure oxygen stream to provide the desired final oxygen concentration in the hyperoxic air provided to the breathing subject, the nitrogen-removal units of this embodiment provide the same desired final oxygen concentrations by selectively removing nitrogen from an air stream to increase the oxygen level from an initial 20–21 volume percent to 22–90 volume percent, more typically to 25–70 volume percent oxygen, and most typically to about 60 volume percent oxygen.

In other embodiments, the present invention provides methods for breathing under hyperoxic conditions based on using the various hyperoxic breathing systems described above. For example, in one embodiment the method involves (a) providing an oxygen source, (b) providing a hyperoxic air stream comprising from about 22 to about 90 volume percent oxygen by mixing ambient air with an oxygen stream from the oxygen source by placing a venturi valve in the oxygen stream, where the venturi valve is configured to introduce the ambient air into the oxygen stream, (c) activating flow of the hyperoxic air stream to a breathing interface by actuating a demand flow valve configured to sense a decrease in pressure at the breathing interface, where the demand flow valve is further configured to cause flowing of oxygen from the oxygen source to the venturi valve, and (d) providing the hyperoxic air stream to a breathing subject by coupling the breathing subject with the breathing interface, typically by use of a breathing mask.

In another embodiment, the method for breathing under hyperoxic conditions involves (a) providing an air source, (b) providing a hyperoxic air stream comprising from about 22 to 90 volume percent oxygen by passing air through a nitrogen-removal unit, (c) activating flow of the hyperoxic air stream to a breathing interface by actuating a demand flow valve configured to sense a decrease in pressure at the breathing interface, where the demand flow valve is further configured to cause flowing of air from the air source to the nitrogen-removal unit, and (d) providing the hyperoxic air stream to a breathing subject by coupling the breathing subject with the breathing interface.

In a further embodiment, the present invention provides a method for increasing caloric expenditure of an exercising subject involving the following steps: (a) generating a hyperoxic air stream comprising 22 to 90 volume percent oxygen by mixing ambient air with an oxygen stream from an oxygen source comprising placing a venturi valve into the oxygen stream where the venturi valve is configured to introduce the ambient air into the oxygen stream, (b) activating flow of the hyperoxic air stream to a breathing interface by actuating a demand flow valve configured to sense a decrease in pressure at the breathing interface, where the demand flow valve is further configured to cause flowing of oxygen from the oxygen source to the venturi valve, and (c) providing the hyperoxic air stream to the exercising subject by coupling the exercising subject with the breathing interface for at least some portion of time spent by the exercising subject in an exercise period.

DETAILED DESCRIPTION OF THE INVENTION

Under most conditions, ambient air is about 20–21 volume percent oxygen and approximately 78 volume percent nitrogen. For purposes of the present invention, hyperoxic air is any oxygen/nitrogen mixture with greater than 21 volume percent oxygen and less than about 78 volume percent nitrogen. Typically, hyperoxic air mixtures useful in the present invention include gaseous mixtures containing 22 to 90 volume percent oxygen, more typically from 25 to 70 volume percent oxygen, and most typically about 60 volume percent oxygen.

Oxygen sources useful in the hyperoxic breathing systems of the present invention include, for example, compressed oxygen containers (such as gas cylinders) and oxygen generation apparatus such as chemical oxygen generators (for example, potassium chlorate or sodium chlorate canisters) and water electrolysis devices. Typically, the oxygen source is provided by high pressure oxygen cylinders (compressed gas). Air sources useful in the hyperoxic breathing systems of the present invention include, for example, compressed air containers (such as gas cylinders) and ambient air.

Nitrogen-removal units suitable for use in the present invention include apparatus or equipment such as nitrogen scrubbers or oxygen concentrator modules. For example, oxygen concentrator technology includes systems that pass compressed air through a series of molecular sieve beds (such as zeolite adsorbents) where the nitrogen is selectively adsorbed relative to the oxygen, and an oxygen-enriched gas stream is provided in the gas effluent from the molecular sieve adsorption beds. Alternatively, systems involving selective gas-permeable membranes may be used to enhance the oxygen concentration from an initial gas stream of air.

The hyperoxic breathing system of the present invention provides hyperoxic air streams to a breathing subject at flow rates adequate to match ventilation rates of the user. These flow rates may vary depending upon the magnitude of the workload taken on by the breathing subject. Ventilation volumes of the users may range from as low as 50 liters/minute (l/min) at the beginning of an exercise period, to as much as 300 l/min or more during heavy exercise.

In the following detailed description of various embodiments of the present invention, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
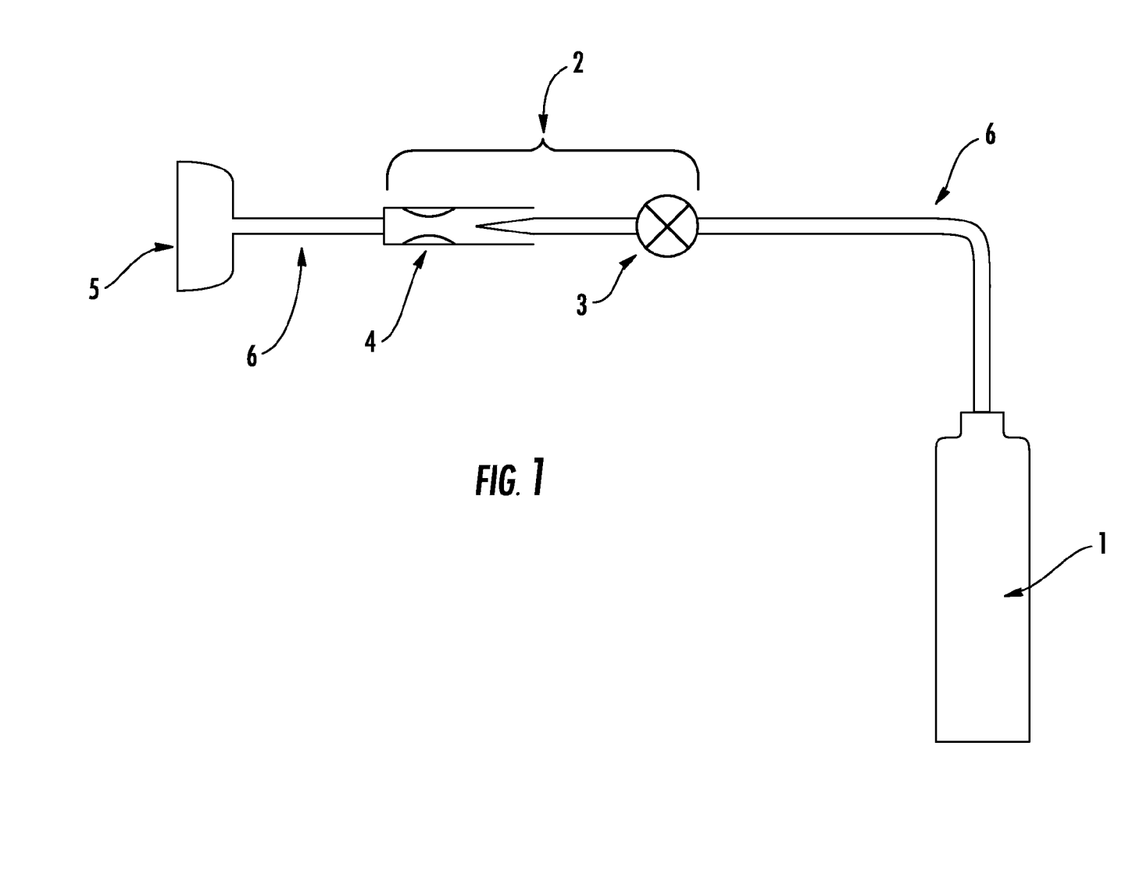
FIG. 1 is a side view of one embodiment of the present invention including an oxygen source, a control valve system and a breathing interface.

In FIG. 1, the oxygen source 1 is provided by a compressed oxygen gas cylinder; other oxygen sources also may be used as previously discussed. The control valve system 2 is made up of demand flow valve 3 and venturi valve 4 (air entrainment valve). Control valve system 2 is coupled to a breathing interface 5. Venturi valve 4 is shown open to atmospheric air and is configured to introduce air into the oxygen stream flowing from oxygen source 1 to breathing interface 5. Gas transport connections 6 provide flow lines for the various gases from point to point, for example, flexible plastic tubing may be used as the gas transport connections. An additional gas transport connection 6 (not shown) may be used to provide communication between flow valve 3 and breathing interface 5.

Figure 1A:
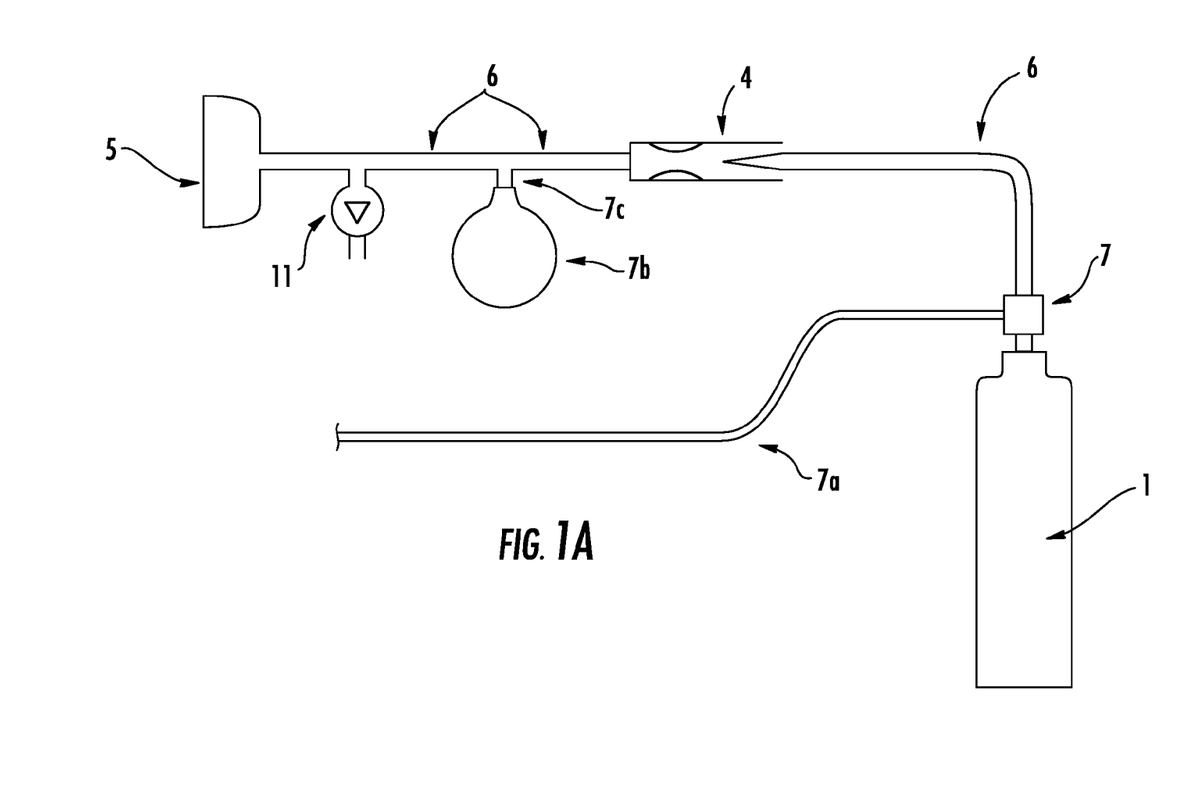
FIG. 1A is a side view of another embodiment of the present invention including an expandable reservoir bag.

In FIG. 1A, oxygen source 1 is shown coupled to a pressure regulator 7 which is further connected to venturi valve 4 and ultimately to breathing interface 5. Expandable reservoir 7b is located (joined to gas transport connection 6 by outlet 7c) between venturi valve 4 and breathing interface 5. One-way exhaust valve 11 is located between expandable reservoir 7b and breathing interface 5. An optional control linkage 7a (such as a cable) may be provided in association with pressure regulator 7 to control the flow rate of oxygen by a breathing subject. Expandable reservoir 7b may be provided in the form of flexible bag having a volume, for example, from 25 to about 50 liters. The expandable reservoir 7b stores the hyperoxic air stream provided by the influx of air by venturi valve 4 into the oxygen stream for use by the breathing subject. One-way exhaust valve 11 would provide for exhaling by the breathing subject.

Figure 2:
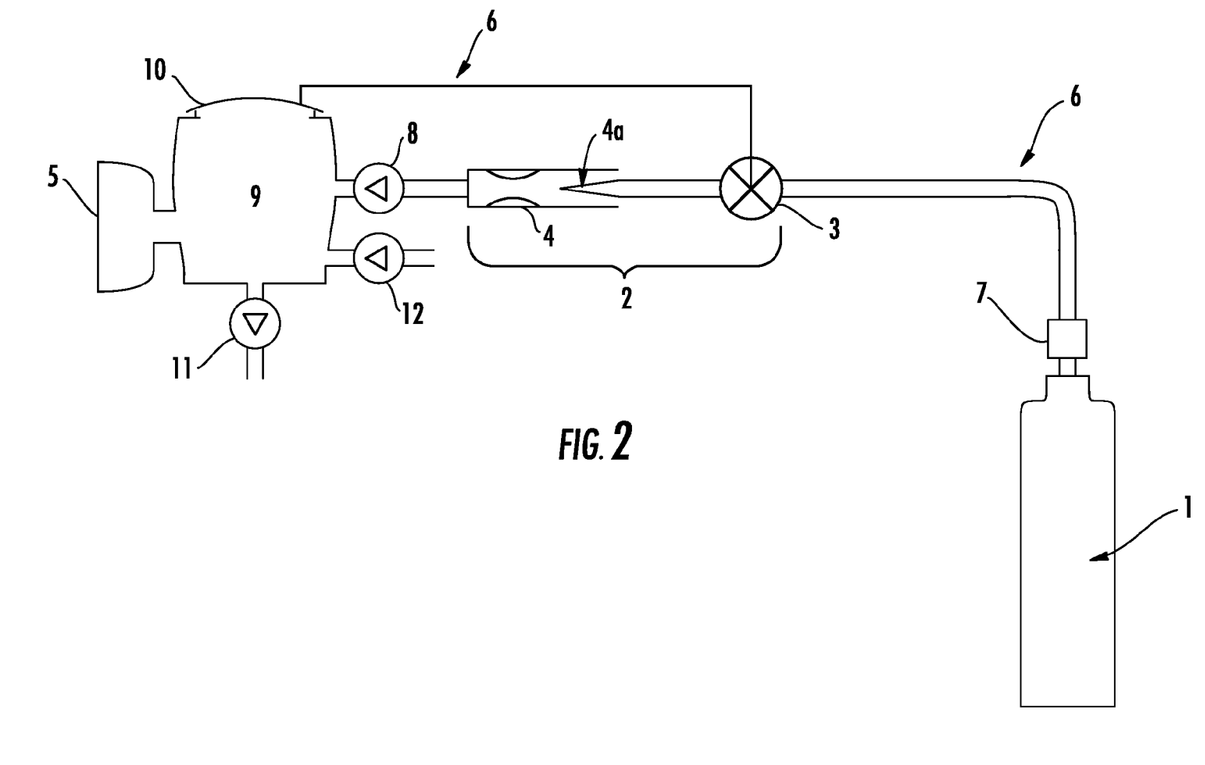
FIG. 2 is a side view of another embodiment of the present invention including a plenum and a one-way flow valve.

FIG. 2 presents a more detailed description of another embodiment of the present invention. A pressure regulator 7 is coupled to oxygen source 1. In this embodiment, a one-way control valve 8 is situated after the control valve system (made up demand flow valve 3 and venturi valve 4) and leads into plenum 9. Plenum 9 includes a diaphragm 10, exhaust valve 111 and emergency valve 12, the latter being used in case of gas flow failure from the oxygen source. One of the gas transport connections 6 provides communication between demand flow valve 3 and plenum 9 through diaphragm 10. Pressure regulator 7 may be further associated with a control linkage (not shown), such as a cable, so that the flow rate of oxygen from oxygen source 1 may be controlled to a desirable level. Use of the control linkage would enable an exercising subject to open or close the pressure regulator from a distance, for example, from a bicycle or a treadmill.

As shown in FIG. 2, pressure regulator 7 acts to step down the pressure from the high pressure of the compressed oxygen gas cylinder 1. The breathing subject would inhale through a breathing mask (not shown) attached to breathing interface 5, decreasing the pressure in plenum 9 and flexing diaphragm 10. The flexing of diaphragm 10 actuates demand flow valve 3 which allows the oxygen to flow at a variable rate to venturi valve 4. At venturi valve 4, oxygen is passed through a nozzle 4a creating a low-pressure area, which draws ambient air into the flowing oxygen stream. The resultant hyperoxic air stream then passes through one-way valve 8, through plenum 9, through breathing interface 5, and on to the breathing subject. As the breathing subject exhales, pressure in plenum 9 increases, the flow of oxygen from oxygen source 1 stops and one-way exhaust valve 11 opens to allow the exhaled breath to exit plenum 9. Should oxygen be depleted at anytime, that is, no oxygen flow from oxygen source 1, emergency valve 12 would open at a slightly higher pressure than was required for diaphragm 10 to actuate demand flow valve 3, allowing the breathing subject to breathe ambient air.

Figure 3:
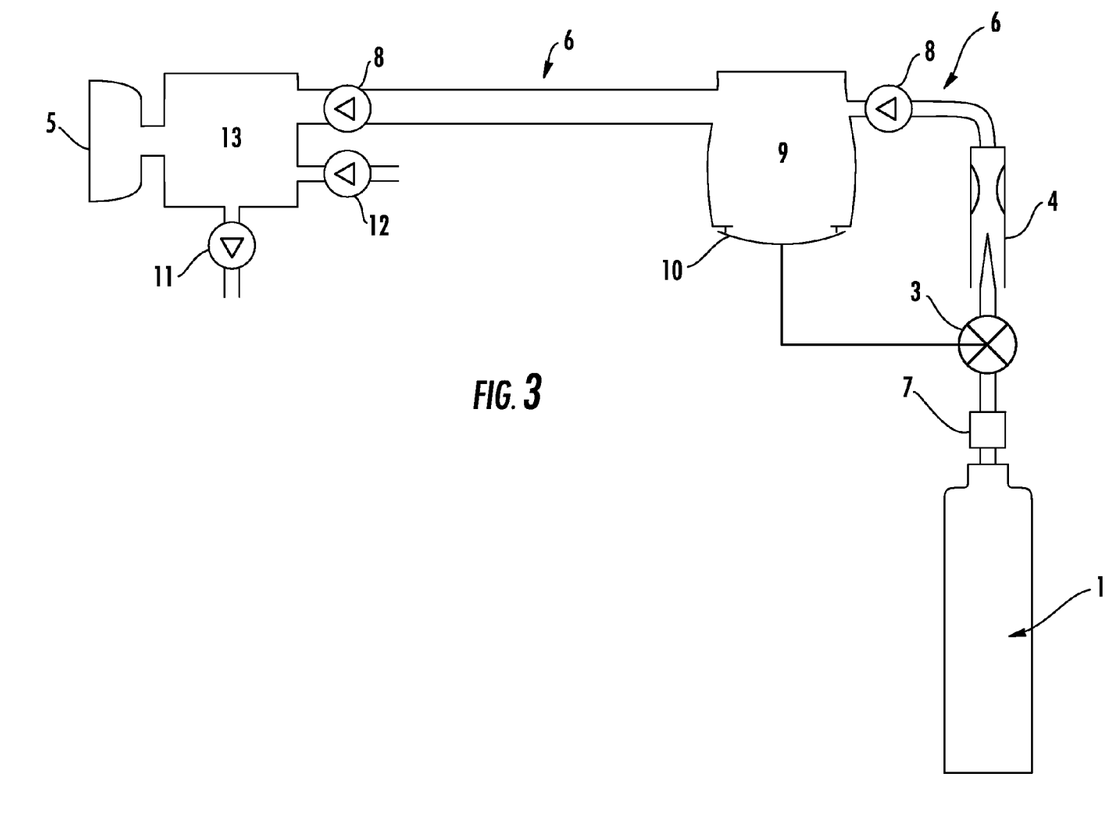
FIG. 3 is a side view of another embodiment of the present invention including a second plenum.

FIG. 3 presents yet another embodiment of the present invention which includes a second plenum 13 located between first plenum 9 and breathing interface 5.

Figure 4:
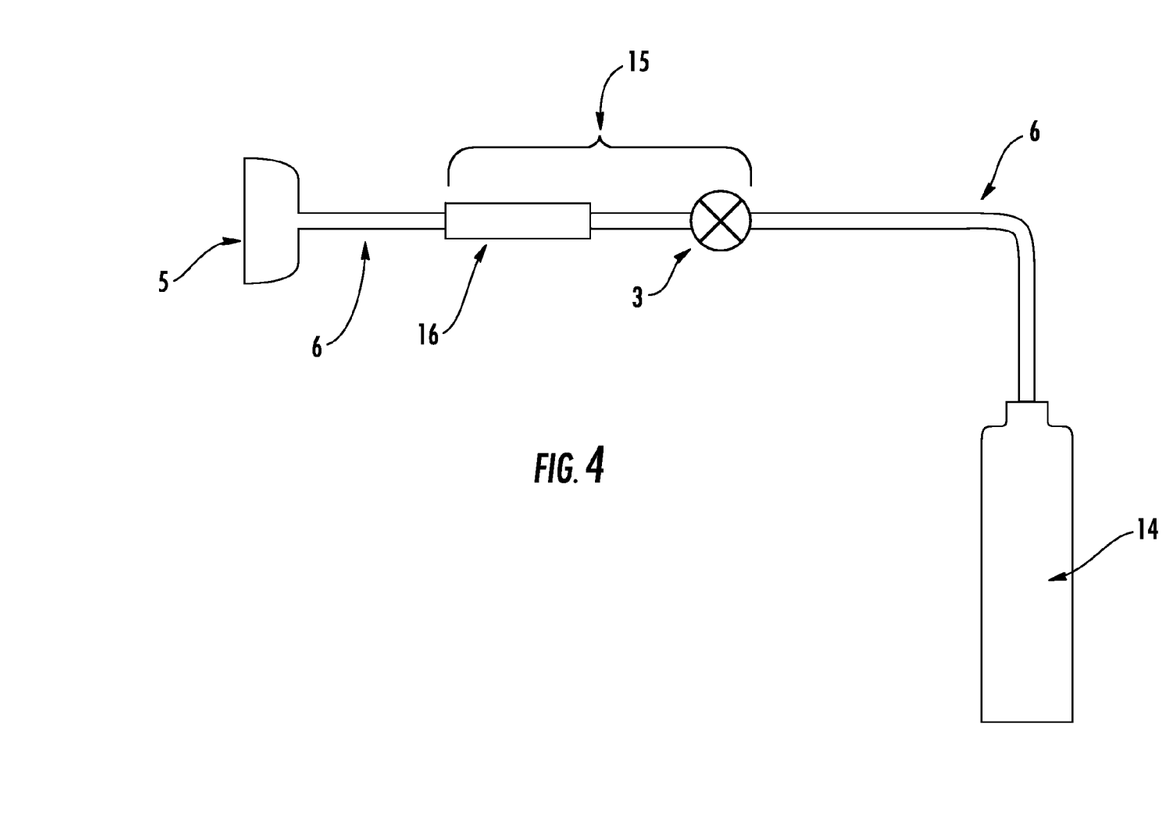
FIG. 4 is a side view of another embodiment of the present invention including a nitrogen-removal unit as part of the control valve system.

FIG. 4 depicts a further embodiment of the present invention where the breathing system includes an air source 14, shown here as a compressed air gas cylinder; however, the air source also may be ambient air. Control valve system 15 includes demand flow valve 3 and nitrogen-removal unit 16. Suitable nitrogen-removal units include, for example, nitrogen scrubbers or oxygen concentrator modules, as discussed above. Control valve system 15 is further connected to breathing interface 5 in similar fashion to that described in FIGS. 1–3. Optional one-way flow valves (not shown) and plenums (not shown) may also be included in similar fashion to that described in FIGS. 1–3.

Optionally, a dual intake valve may be placed between control valve systems 2 or 15 and breathing interface 5 components of the breathing systems shown in FIGS. 1–4 in order to mix additional ambient air into the hyperoxic air stream, as desired.

An additional optional feature may include the use of computer software programmed with various warning alarms and interfacing with any breathing apparatus used by a breathing subject, for example an exercising individual. Pulmonary functions (such as inhalation and heart rates, blood oxygen level and inhaled and exhaled oxygen concentrations) may be monitored through a computer/software interface such that automatic changes in hyperoxic air stream flow could be actuated via the pressure regulator associated with the oxygen source. Sensors in the expandable reservoir (such as fiber optic sensors) could further monitor the level of hyperoxic air in the reservoir and be interfaced with appropriate computer software to actuate changes in flow from the oxygen source.

An additional optional feature of the present invention may include a humidifier device located in the system prior to the breathing interface. In this way hyperoxic air provided by the breathing system of the present invention could be humidified to a desired level to help decrease dehydration during physical training of an individual.

Although the description above contains many specifications, these should not be construed as limiting the scope of the invention but as merely providing illustrations of some of various embodiments of this invention. Thus, the scope of the invention should be determined by the appended claims and their legal equivalents rather than by the examples given.

We claim:

1. A hyperoxic breathing system comprising:
   (a) an oxygen source;
   (b) a control valve system coupled to the oxygen source, the control valve system comprising a demand flow valve and a venturi valve configured to introduce ambient air;
   (c) a breathing interface coupled to the control valve system;
   (d) a one-way flow valve located between the venturi valve and the breathing interface; and
   (e) a plenum coupled to the control valve system via the one-way flow valve, wherein the plenum further comprises at least one exhaust valve for relieving excess pressure within the plenum to ambient atmosphere.

2. The hyperoxic breathing system of claim 1 wherein the demand flow valve and the venturi valve are connected in series, the oxygen source is coupled to the control valve system through the demand flow valve, and the venturi valve is located between the demand flow valve and the breathing interface.

3. The hyperoxic breathing system of claim 1 wherein the plenum further comprises a diaphragm and the plenum is in communication with the demand flow valve via a gas transport connection.

4. The hyperoxic breathing system of claim 1 further comprising a breathing mask configured to provide hyperoxic air to a breathing subject and attached to the breathing interface.

5. The hyperoxic breathing system of claim 1 further comprising a pressure regulator, coupled to the oxygen source and located between the oxygen source and the control valve system, for controlling oxygen pressure.

6. The hyperoxic breathing system of claim 5 further comprising a control linkage associated with the pressure regulator and configured to control oxygen flow from the oxygen source.

7. The hyperoxic breathing system of claim 1 wherein the oxygen source is selected from the group consisting of a compressed oxygen container and an oxygen generation apparatus.

8. A hyperoxic breathing system comprising:
(a) an oxygen source;
(b) a control valve system coupled to the oxygen source, the control valve system comprising a demand flow valve and a venturi valve configured to introduce ambient air;
(c) a breathing interface coupled to the control valve system;
(d) a one-way flow valve located between the venturi valve and the breathing interface; and
(e) a plenum coupled to the control valve system via the one-way flow valve, wherein the plenum further comprises at least one valve for emergency access to ambient air.

* * * * *